United States Patent [19]

Bachovchin et al.

[11] Patent Number: 5,462,928

[45] Date of Patent: Oct. 31, 1995

[54] INHIBITORS OF DIPEPTIDYL-AMINOPEPTIDASE TYPE IV

[75] Inventors: William W. Bachovchin, Melrose; Andrew G. Plaut; Flentke George R., both of Boston, all of Mass.

[73] Assignees: New England Medical Center Hospitals, Inc., Boston; Tufts University, Medford, both of Mass.

[21] Appl. No.: 93,302

[22] Filed: Jul. 15, 1993

Related U.S. Application Data

[63] Continuation of Ser. No. 781,552, Oct. 22, 1991, abandoned, which is a continuation-in-part of Ser. No. 510,274, Apr. 14, 1990, abandoned.

[51] Int. Cl.[6] ........................ A61K 38/00; A61K 31/675; A01N 57/00; A01N 65/00
[52] U.S. Cl. ........................ 514/19; 514/16; 514/17; 514/18; 514/85; 514/89; 514/69; 514/210
[58] Field of Search .................... 514/16–19, 85, 514/89, 69, 210

[56] References Cited

U.S. PATENT DOCUMENTS 4,935,493  6/1990  Bachovchin et al. ............... 530/331

OTHER PUBLICATIONS

Blumenstein et al, Biochem. Biophys. Res. Comm. vol. 163, pp. 980–987.
ASM News vol. 56 p. 368 (1990).

*Primary Examiner*—Jill Warden
*Assistant Examiner*—Sheera J. Huff
*Attorney, Agent, or Firm*—Fish & Richardson

[57] ABSTRACT

The invention features an inhibitor of DP-IV, having the structure:

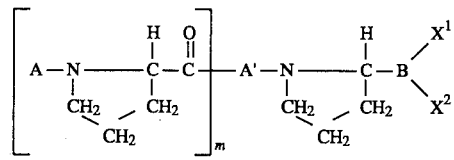

wherein m is an integer between 0 and 10, inclusive; A and A' are L-amino acid residues such that the A in each repeating bracketed unit can be a different amino acid residue; the C bonded to B is in the L-configuration; the bonds between A and N, A' and C, and between A' and N are peptide bonds; and each $X^1$ and $X^2$ is, independently, a hydroxyl group or a group capable of being hydrolyzed to a hydroxyl group at physiological pH.

13 Claims, 2 Drawing Sheets

R=H,CH₃ n=1-3

R=alkyl (C₁ C₃),H
n=1-3 n=2-4

INHIBITORS OF DIPEPTIDYL-AMINOPEPTIDASE TYPE IV

CROSS REFERENCE TO RELATED APPLICATIONS

This application is a continuation of U.S. application Ser. No. 07/781,552, filed Oct. 22, 1991, now abandoned, which in turn is a continuation-in-part of U.S. application Ser. No. 07/510,274, filed Apr. 14, 1990, now abandoned.

BACKGROUND OF THE INVENTION

This invention relates to inhibitors of the amino peptidase activity of dipeptidyl peptidase type IV (DP-IV).

DP-IV is a postproline cleaving enzyme with a specificity for removing Xaa-Pro (where Xaa represents any amino acid) dipeptides from the amino terminus of polypeptides. DP-IV will also remove Xaa-Ala dipeptides from amino termini, albeit less efficiently. DP-IV is present in many mammalian cells and tissues, for example, renal tubule cells, intestinal epithelium, and blood plasma. It is also present on the surface of CD4+ and some CD8+ T-cells. It is thought to be involved in the regulation of the immune response; occurrence of DP-IV on a cell surface is associated with the ability of cells to produce interleukin-2 (IL-2). DP-IV is also referred to as dipeptidyl-peptide hydrolase DAP-IV or DPP-IV; it is assigned EC number 3.4.14.5.

Three different inhibitors of DP-IV are known. One of these is a suicide inhibitor: N-Ala-Pro-O-(nitrobenzyl-) hydroxylamine. (The standard three letter amino acid codes are used in this application; O represents oxygen.) Another is a competitive inhibitor: e-(4-nitro) benzoxycarbonyl-Lys-Pro. The third is a polyclonal rabbit anti-porcine kidney DP-IV immunoglobulin.

SUMMARY OF THE INVENTION

The enzymatic activity of DP-IV involves cleaving of a dipeptide from the free amino terminus of a polypeptide. DP-IV has a preference for cleaving after a proline, i.e., a proline in the penultimate position from the amino terminus. A free amino terminus is required; thus, DP-IV is a post-proline cleaving enzyme with a specificity for removing an N-terminal Xaa-Pro dipeptide from a polypeptide (where Xaa can be any amino acid, including proline). DP-IV also will remove a Xaa'-Ala dipeptide from an amino terminus of a polypeptide when Xaa' is an amino acid with a bulky side group, e.g., tyrosine.

This invention concerns provision of potent inhibitors of the enzymatic activity of DP-IV. Generally, an α-amino boronic acid analog of proline (boroPro is used to designate one such analog which has the carboxyl group of proline replaced with a $B(OH)_2$ group, where $(OH)_2$ represents two hydroxyl groups and B represents boron) is bonded to an amino acid to form a dipeptide with boroPro as the carboxy terminal residue. These dipeptide prolyl-boronic acids are potent and highly specific inhibitors of DP-IV, with $K_i$ values in the nanomolar range.

Dipeptides having the boroPro moiety are relatively unstable; thus, we have designed inhibitors having at least two other amino acid residues. Generally, the structure of these inhibitors is X-Pro-Y-boroPro where X and Y are chosen from any amino acid residue (including proline). This tetrapeptide may be lengthened at its amino-terminus by addition of one or more dipeptides, each dipeptide having the general formula Z-Pro or Z-ala, where each Z independently is any amino acid residue (including proline). This general structure is defined in more detail below. These inhibitors function as inhibitors of DP-IV because each dipeptide portion is a substrate for DP-IV and the final product of the reaction of such an inhibitor with DP-IV is the dipeptide inhibitor Y-boroPro. The amino terminus of these inhibitors must not be blocked or they lose their inhibitory capacity for DP-IV, since DP-IV cannot cleave a dipeptide from a blocked N-terminal polypeptide.

Thus, in a first aspect, the invention features an inhibitory compound having the structure: Group I–Group II. Group I has the structure:

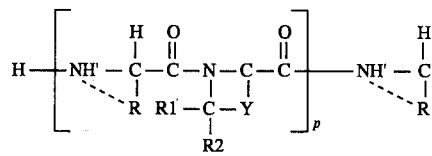

where H represents a hydrogen; C represents a carbon; O represents an oxygen; N represents a nitrogen; each R, independently, is chosen from the group consisting of the R groups of an amino acid, including proline; each broken line, independently, represents a bond to an H or a bond to one R group, and each H' represents that bond or a hydrogen; and p is an integer between 0 and 4 inclusive. Alternatively, Group I has the structure:

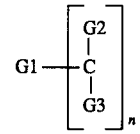

where n is between 0 and 3 inclusive, each G2 and G3 independently is H or C1–3 (one to three carbon atoms) alkyl, G1 is NH3 (H3 represents three hydrogens),

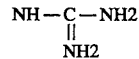

(H2 represents two hydrogens), or NG4, where G4 is

where G5 and G6 can be NH, H, or C1–3 alkyl or alkenyl with one or more carbons substituted with a nitrogen. G1 bears a charged, and G1 and Group II do not form a covalently bonded ring structure at pH 7.0. Group I may also have the structure:

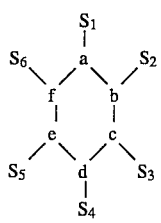

where one or two of the a, b, c, d, e, and f group is N, and the rest are C, and each S1–S6 independently is H or C1–C3 alkyl. Group I may also include a five membered unsaturated ring having two nitrogen atoms, e.g., an imidazole ring. Group II has the structure:

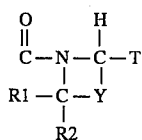

where T is a group of the formula:

where each D1 and D2, independently, is a hydroxyl group or a group which is capable of being hydrolysed to a hydroxyl group in aqueous solution at physiological pH; a group of the formula:

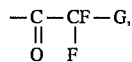

where G is either H, fluorine (F) or an alkyl group containing 1 to 20 carbon atoms and optional heteroatoms which can be N, S (sulfur), or O; or a phosphonate group of the formula:

where each J, independently, is O-alkyl, N-alkyl, or alkyl. Each O-alkyl, N-alkyl or alkyl includes 1–20 carbon atoms and, optionally, heteroatoms which can be N, S, or O. T is generally able to form a complex with the catalytic site of a DP-IV.
Y is

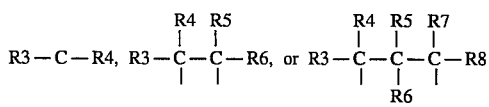

and each R1, R2, R3, R4, R5, R6, R7, and R8, separately is a group which does not significantly interfere with site specific recognition of the inhibitory compound by DP-IV, and allows a complex to be formed with DP-IV.

In preferred embodiments, T is a boronate group, a phosphonate group or a trifluoroalkyl ketone group; each R1–R8 is H; each R1 and R2 is H, and each Y is the $CH_2$—$CH_2$; each R is independently chosen from the R group of proline and alanine; the ihibitory compound has a binding or dissociation constant to DP-IV of at least $10^{-9}M$, $10^{-8}M$ or even $10^{-7}M$; the inhibitory compound is admixed with a pharmaceutically acceptable carrier substance; and each D1 and D2 is, independently, F, or D1 and D2 together are a ring containing 1 to 20 carbon atoms, and optionally heteroatoms which can be N, S, or O.

In a second aspect, the invention features a method for inhibiting the enzymatic activity of DP-IV in a mammal. The method includes administering to the mammal an effective amount of an inhibitory compound described above. Most preferably, the amount of compound administered is between 1 and 500 mg/kilogram of animal treated/day.

In a third aspect, the invention features an inhibitor of DP-IV, having the structure:

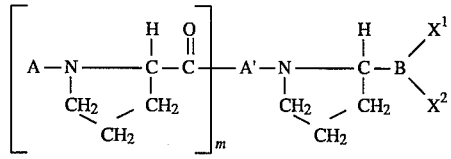

wherein m is an integer between 0 and 10, inclusive; A and A' are L-amino acid residues (for glycine there is no such distinction) such that the A in each repeating bracketed unit can be a different amino acid residue; the C bonded to B is in the L-configuration; the bonds between A and N, A' and C, and between A' and N are peptide bonds; and each $X^1$ and $X^2$ is, independently, a hydroxyl group or a group capable of being hydrolysed to a hydroxyl group at physiological pH. By "the C bonded to B is in the L-configuration" is meant that the absolute configuration of the C is like that of an L-amino acid.

Thus the

group has the same relationship to the C as the —COOH group of an L-amino acid has to its α carbon. In various preferred embodiments, A and A' are independently proline or alanine residues; m is 0; $X^1$ and $X^2$ are hydroxyl groups; the inhibitor is L-Ala-L-boroPro; and the inhibitor is L-Pro-L-boroPro.

In a fourth aspect, the invention features a method for inhibiting DP-IV in a mammal. The method includes administering to the mammal an effective amount of the compound:

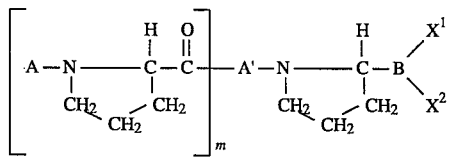

described above. In a preferred embodiment, the amount is 1 mg/kg of the mammal per day to 500 mg/kg of the mammal per day.

Other features and advantages of the invention will be apparent from the following description of the preferred embodiments, and from the claims.

DESCRIPTION OF THE PREFERRED EMBODIMENTS

The drawings will first be briefly described.

Figure 1:
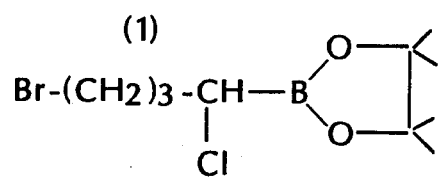
Figure 1:
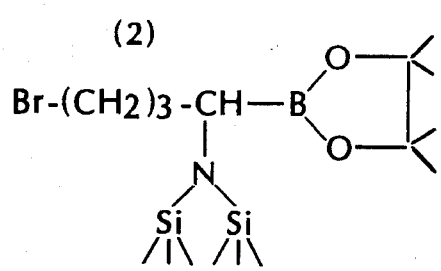
Figure 1:
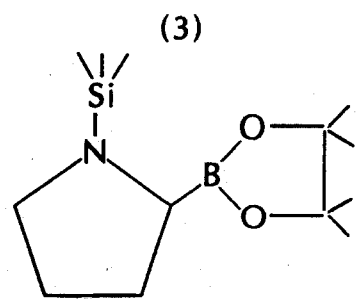
Figure 1:
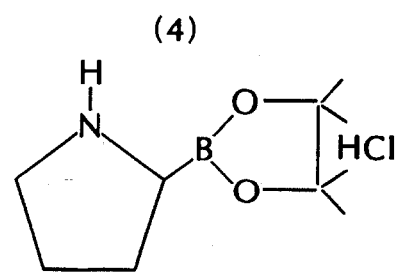
Figure 1:
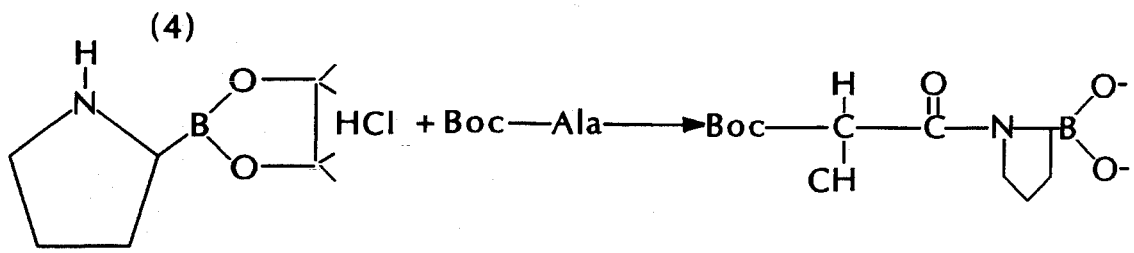
Figure 2:
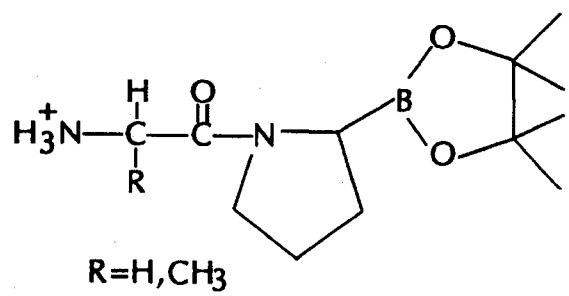
Figure 2:
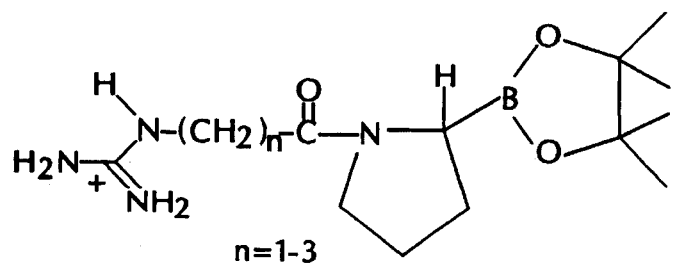
Figure 2:
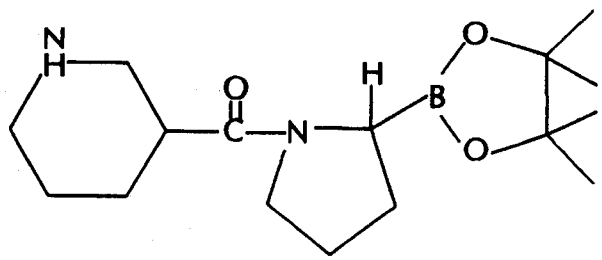
Figure 2:
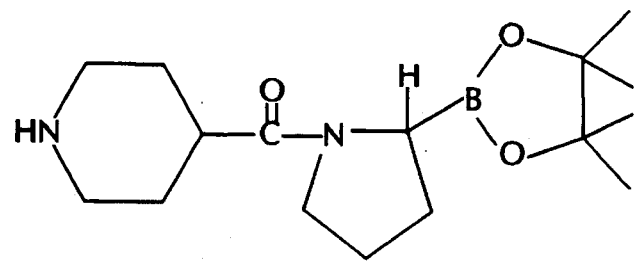
Figure 2:
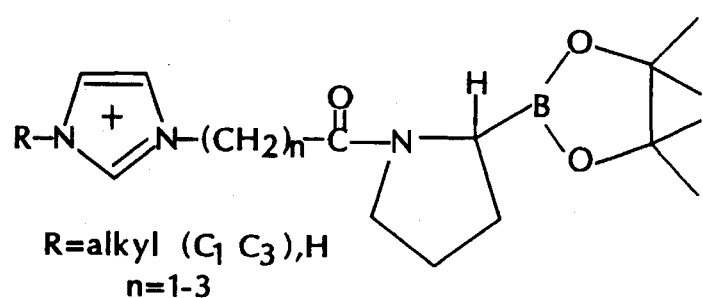
Figure 2:
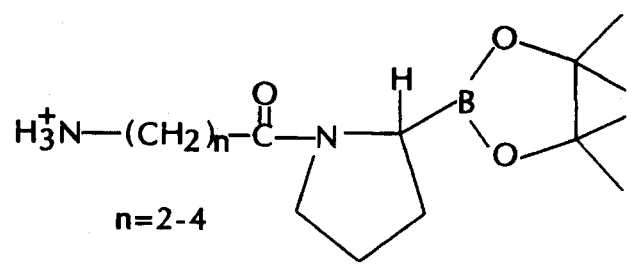

Drawings FIG. 1 is a diagrammatic representation of the synthesis of a boro proline compound; and FIG. 2 is a diagrammatic representation of several embodiments of the invention.

Structure

The inhibitory compounds of the invention have the general structure recited in the Summary of the Invention above. Examples of preferred structures are those referred to as preferred embodiments above.

The structure of the preferred inhibitory compounds is such that at least a portion of the amino acid sequence near the cleavage site of a DP-IV substrate is duplicated, or nearly duplicated. This duplication is in part responsible for the ability of the inhibitory compounds to inhibit DP-IV, by a mechanism thought to involve competitive inhibition between a DP-IV inhibitory compound or a DP-IV cleavage product of the inhibitory compound, and the actual DP-IV substrate.

The choice of amino acid sequence affects the inhibitory activity of the inhibitory compound, and its specificity. Peptide fragments can be synthesized and then tested to determine their efficacy as inhibitors, using standard techniques. Specificity is determined in a similar fashion, by testing the inhibitory effect of a particular inhibitory compound on the enzyme activity. The inhibitory compounds preferably inhibit the enzymatic activity of DP-IV and do not inhibit enzymes necessary for normal cell functions.

The inhibitory compounds include a group (T) which causes the inhibitory compound to complex with DP-IV, not only in a competitive fashion, but in a chemically reactive manner to form a strong bond between the inhibitory compound and DP-IV. This group thus acts to bind the inhibitory compound to DP-IV, and increases the inhibitory binding constant ($K_i$) of the inhibitory compound. Examples of such groups include boronates, fluoroalkyl ketones and phosphoramidates (of the formulae given in the Summary above). These groups are covalently bonded to the prolyl residue of the compound, as in the above formula.

The proline or proline analog, represented by

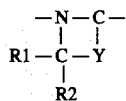

above, is chosen so that it mimics the structure of proline recognized by the active site of DP-IV. It can be modified by providing R1 and R2 groups which do not interfere significantly with this recognition, and thus do not significantly affect the $K_i$ of the compound. Thus, one or more hydroxyl groups can be substituted to form hydroxyproline, and methyl or sugar moieties may be linked to these groups. One skilled in the art will recognize that these groups are not critical in this invention and that a large choice of substituents are acceptable for R1 and R2. In part, the requirement that the above described proline analog mimics the structure of proline recognized by the active site of DP-IV means that the C bonded to N and Y has the same stereochemistry as the alpha carbon of L-proline.

Synthesis of BoroProline

Referring to FIG. 1, the starting compound I is prepared essentially by the procedure of Matteson et al. (*Organometallics* 3:1284, 1984), except that a pinacol ester is substituted for the pinanediol ester. Similar compounds such as boropipecolic acid and 2-azetodine boronic acid can be prepared by making the appropriate selection of starting material to yield the pentyl and propyl analogs of compound I. Further, Cl can be substituted for Br in the formula, and other diol protecting groups can be substituted for pinacol in the formula, e.g., 2, 3-butanediol and alphapinanediol.

Compound II is prepared by reacting compound I with $[(CH_3)O_3Si]_2N\text{-}Li+$. In this reaction hexamethyldisilazane is dissolved in tetrahydrofuran and an equivalent of n-butyllithium added at $-78°$ C. After warming to room temperature ($20°$ C.) and cooling to $-78°$ C., an equivalent of compound I is added in tetrahydrofuran. The mixture is allowed to slowly come to room temperature and to stir overnight. The alpha-bis[trimethylsilane]-protected amine is isolated by evaporating solvent and adding hexane under anhydrous conditions. Insoluble residue is removed by filtration under a nitrogen blanket, yielding a hexane solution of compound II.

Compound III, the N-trimethysilyl protected form of boroProline is obtained by the thermal cyclization of compound II during the distillation process in which compound II is heated to $100°\text{–}150°$ and distillate is collected which boils $66°\text{–}62°$ C. at 0.06–0.10 mm pressure.

Compound IV, boroProline-pinacol hydrogen chloride, is obtained by treatment of compound III with HCl:dioxane. Excess HCl and by-products are removed by trituration with ether. The final product is obtained in a high degree of purity by recrystallization from ethyl acetate.

The boroProline esters can also be obtained by treatment of the reaction mixture obtained in the preparation of compound II with anhydrous acid to yield 1-amino-4-bromobutyl boronate pinacol as a salt. Cyclization occurs after neutralizing the salt with base and heating the reaction.

Preparation of boroProline-pinacol

The intermediate, 4-Bromo-1-chlorobutyl boronate pinacol, was prepared by the method in Matteson et al. (*Organometallics* 3:1284, 1984) except that conditions were modified for large scale preparations and pinacol was substituted for the pinanediol protecting group.

3-bromopropyl boronate pinacol was prepared by hydrogenboronation of allyl bromide (173 ml, 2.00 moles) with catechol borane (240 ml, 2.00 moles). Catechol borane was added to allyl bromide and the reaction heated for 4 hours at $100°$ C. under a nitrogen atmosphere. The product, 3-bromopropyl boronate catechol (bp $95°\text{–}102°$ C., 0.25 mm), was isolated in a yield of 49% by distillation. The catechol ester (124 g, 0.52 moles) was transesterified with pinacol (61.5 g, 0.52 moles) by mixing the component in 50 ml of THF and allowing them to stir for 0.5 hours at $0°$ C. and 0.5 hours at room temperature. Solvent was removed by evaporation and 250 ml of hexane added. Catechol was removed as a crystalline solid. Quantitative removal was achieved by successive dilution to 500 ml and to 1000 ml with hexane and removing crystals at each dilution. Hexane was evaporated and the product distilled to yield 177 g (bp $60°\text{–}64°$ C., 0.35 mm).

4-Bromo-1-chlorobutyl boronate pinacol was prepared by homologation of the corresponding propyl boronate. Methylene chloride (50.54 ml, 0.713 moles) was dissolved in 500 ml of THF, 1.54N n-butyllithium in hexane (480 ml, 0.780 moles) was slowly added at $-100°$ C. 3-Bromopropyl boronate pinacol (178 g, 0.713 moles) was dissolved in 500 ml of THG, cooled to the freezing point of the solution, and added to the reaction mixture. Zinc chloride (54.4 g, 0.392 moles) was dissolved in 250 ml of THG, cooled to $0°$ C., and added to the reaction mixture in several portions. The reaction was allowed to slowly warm to room temperature and to stir overnight. Solvent was evaporated and the residue dissolved in hexane (1 liter) and washed with water (1 liter). Insoluble material was discarded. After drying over anhydrous magnesium sulfate and filtering, solvent was evaporated. The product was distilled to yield 147 g (bp 110°–112° C., 0.200 mm).

N-Trimethylsilyl-boroProline pinacol was prepared first by dissolving hexamethyldisilizane (20.0 g, 80.0 mmoles) in 30 ml of THF, cooling the solution to −78° C., and adding 1.62N n-butyllithium in hexane (49.4 ml, 80.0 mmoles). The solution was allowed to slowly warm to room temperature. It was recooled to −78° C. and 4-bromo-1-chlorobutyl boronate pinacol (23.9 g, 80.0 mmoles) added in 20 ml of THF. The mixture was allowed to slowly warm to room temperature and to stir overnight. Solvent was removed by evaporation and dry hexane (400 ml) added to yield a precipitant which was removed by filbration under a nitrogen atmosphere. The filtrate was evaporated and the residue distilled, yielding 19.4 g of the desired product (bp 60°–62° C., 0.1–0.06 mm).

H-boroProline-pinacol.HCl (boroProline-pinacol.HCl) was prepared by cooling N-trimethylsilyl-boroProline pinacol (16.0 g, 61.7 mmoles) to −78° C. and adding 4N HCL:dioxane 46 ml, 185 mmoles). The mixture was stirred 30 minutes at −78° C. and 1 hour at room temperature. Solvent was evaporated and the residue triturated with ether to yield a solid. The crude product was dissolved in chloroform and insoluble material removed by filtration. The solution was evaporated and the product crystallized from ethyl acetate to yield 11.1 g of the desired product (mp 156.5°–157° C.).

Synthesis of boroProline Peptides

General methods of coupling of N-protected peptides and amino acids with suitable side-chain protecting groups to H-boroProline-pinacol are applicable. When needed, side-chain protecting and N-terminal protecting groups can be removed by treatment with anhydrous HCl, HBr, trifluoroacetic acid, or by catalytic hydrogenation. These procedures are known to those skilled in the art of peptide synthesis.

The mixed anhydride procedure of Anderson et al. (*J. Am. Chem. Soc.* 89:5012, 1984) is preferred for peptide coupling. Referring again to FIG. 1, the mixed anhydride of an N-protected amino acid or a peptide is prepared by dissolving the peptide in tetrahydrofuran and adding one equivalent of N-methylmorpholine. The solution is cooled to −20° C. and an equivalent of isobutyl chloroformate is added. After 5 minutes, this mixture and one equivalent of triethylamine (or other sterically hindered base) are added to a solution of H-boroPro-pinacol dissolved in either cold chloroform of tetrahydrofuran.

The reaction mixture is routinely stirred for one hour at −20° C. and 1 to 2 hours at room temperature (20° C.). Solvent is removed by evaporation, and the residue is dissolved in ethyl acetate. The organic solution is washed with 0.20N hydrochloric acid, 5% aqueous sodium bicarbonate, and saturated aqueous sodium chloride. The organic phase is dried over anhydrous sodium sulfate, filtered, and evaporated. Products are purified by either silica gel chromatography or gel permeation chromatography using Sephadex™ LH-20 and methanol as a solvent.

Previous studies have shown that the pinacol protecting group can be removed in situ by preincubation in phosphate buffer prior to running biological experiments (Kettner et al., *J. Biol. Chem.* 259:15106, 1984). Several other methods are also applicable for removing pinacol groups from peptides, including boroProline, and characterizing the final product. First, the peptide can be treated with diethanolamine to yield the corresponding diethanolamine boronic acid ester, which can be readily hydrolyzed by treatment with aqueous acid or a sulfonic acid substituted polystyrene resin as described in Kettner et al. (supra). Both pinacol and pinanediol protecting groups can be removed by treating with BC13 in methylene chloride as described by Kinder et al. (*J. Med. Chem.* 28:1917). Finally, the free boronic acid can be converted to the difluoroboron derivative (—BF2) by treatment with aqueous HF as described by Kinder et al. (supra).

Similarly, different ester groups can be introduced by reacting the free boronic acid with various di-hydroxy compounds (for example, those containing heteroatoms such as S or N) in an inert solvent.

Preparation of H-Ala-boroPro

Boc-Ala-boroPro was prepared by mixed anhydride coupling of the N-Boc-protected alanine and H-boroPro prepared as described above. H-Ala-boroPro (Ala-boroPro) was prepared by removal of the Boc protecting group at 0° C. in 3.5 molar excess of 4N HCl-dioxane. The coupling and deblocking reactions were performed by standard chemical reaction. Ala-boroPro has a $K_i$ for DP-IV of in the nanomolar range. Boc-blocked Ala-boroPro has no affinity for DP-IV.

The two diastereomers of Ala-boroPro-pinacol, L-Ala-D-boroPro-pinacol and L-Ala-L-boroPro-pinacol, can be partially separated by silica gel chromatography with 20% methanol in ethyl acetate as eluant. The early fraction appears by NMR analysis to be 95% enriched in one isomer. Because this fraction has more inhibits DP-IV to a greater extent than later fractions (at equal concentrations) it is probably enriched in the L-boroPro (L-Ala-L-boroPro-pinacol) isomer.

One significant drawback with H-Ala-boroPro as an inhibitor for DP-IV is that is decomposes in aqueous solution at neutral pH and room temperature (20°–25° C.) with a half-life of around 0.5 hour. Many dipeptide derivatives with a free N terminal amino group and a functional group (such as a difluoromethyl ketone) on the C-terminus are similarly unstable due to intramolecular reaction. A six member ring is formed between the amino and C-terminal functional groups and undergoes subsequent further reaction, such as hydrolysis. DP-IV bound inhibitor is more stable, consistent with the hypothesis that decomposition is due to an intramolecular reaction.

H-Pro-boroPro is more stable than H-Ala-boroPro. The $K_i$ of H-Pro-boroPro for DP-IV is about $1 \times 10^{-8}$M and it decomposes in aqueous solution at room temperature (20°–25° C.) with a half life of about 1.5 hours. Although the affinity of H-Pro-boroPro is about 10-fold less than that of H-Ala-boroPro, the increased stability is advantageous.

Because of the relatively short half life of the above dipeptides inhibitory compounds of the invention are formed as tetrapeptides or longer peptides as shown in the general formula above. These inhibitory compounds are substrates for DP-IV yielding the dipeptide inhibitor A'-boroPro. These polypeptide boronic acids are generally stable and can be administered by any standard procedure to act as a substrate for DP-IV and then as a source of a potent DP-IV inhibitor. The advantages of such molecules is that inhibitor is released only in the vicinity of active DP-IV. These polypeptide boronic acids can be made by the method of mixed anhydride coupling by one of ordinary skill in the art, e.g., Mattason (*Organometallics* 3:1284, 1984).

Assays for DP-IV Inhibition

The following are examples of systems by which the inhibitory activity of the above described inhibitory compounds can be tested on DP-IV. As an example H-Ala-boroPro is used to test each of these systems. Inhibitory compounds can be tested by simply substituting them for H-Ala-boroPro.

DP-IV is purified from pig kidney cortex by the method of Barth et al. (*Acta Biol. Med. Germ.* 32:157, 1974) and Wolf et al. (Acta Biol. Med. Germ. 37:409, 1978) and from human placenta by the method of Puschel et al. (*Eur. J. Biochem.* 126:359, 1982). H-Ala-boroPro inhibits both enzymes with a $K_i$ in the nanomolar range.

Human Peripheral blood Mononuclear Cells

H-Ala-boroPro was tested for its influence on PHA-induced proliferation of human peripheral blood mononuclear cells. Human peripheral blood mononuclear cells were obtained from healthy human donors by Ficoll-Hypaque density gradient centrifugation. The cells are washed three times in RPMI 1640 medium and resuspended to a concentration of a $1\times10^6$ in RPMI. 10% human serum was used as necessary.

The proliferative response of lymphocytes was measured using 3H-Thymidine incorporation. $5\times10^3$ MNC cells (Ford in *Handbook of Experimental Immunology*, Weir, ed., Blackwell Scientific Publications, Oxford, 1978) were distributed into wells of round-bottom microtiter plates and incubated in the presence or absence of various dilutions of antigen, mitogen, lymphokine or other agent of interest. Cells were cultured in an atmosphere of 5% $CO_2$ in air for 72 hours after which $^3$H-Thymidine (0.5 µCi/well; 2.0 Ci/mM, New England Nuclear) was added 6 hours before termination of culture. The cells were harvested with a multiple automatic harvester, and $^3$H-thymidine incorporation assessed by liquid scintillation counting. $^3$H thymidine incorporation was determined relative to control values in the absence of inhibitor. Inhibitor was added to give a final concentration of $1\times10^{-4}$M, but lower concentrations can be used.

HIV gene replication

We examined the effect of H-Ala-boroPro on HIV-1 replication in vitro. The rational for these experiments comes from the reported connection between T-cell activation, IL-2 production, and HIV replication and expression of HIV proteins. For example, inductive signals associated with HIV replication include mitogens, antigens, lymphokines, and transcriptions factors such as $NF-_\kappa B$, all of which have been shown to be associated with induction of IL-2 production, T-cell activation, or both.

Cell lines used in the present studies include A3.5 cells (a monocyte cell line which is CD4+, HLA-DR+, and CD3−) and peripheral blood mononuclear cells (PBMC). The A3.5 cells grow continuously in culture without exogenous growth factors. PBMC cells require IL-2 for propagation in vitro. Cells were infected with HIV-1-IIIB at a multiplicity of infection (moi) of $5\times10^{-4}$ tissue culture infectious dose 50 (TCID50)/cell for both the A3.5 cells and the PMBC cells. Dilutions of inhibitor were made in RPMI-1640 and subsequently passed through a 0.22 um filter. At the start of each experiment, $1\times10^6$ cells/well, in 24-well plates, were infected with HIV-1-IIIB at the moi indicated above. Inhibitor was added simultaneously at the appropriate dilutions. All cultures were maintained at 5% $CO_2$ and 37° C. in RPMI-1640 supplemented with penicillin, streptomycin, L-glutamine, hepes buffer, and 20% heat-inactivated fetal calf serum. Cell counts and viability were determined by trypan blue exclusion. Culture supernatants were harvested and assayed for HIV-1 p24 antigen by ELISA (NEN-DuPont, Boston, Mass.). Fresh media and inhibitor were added on each day. For PBMC cultures, cells were collected from HIV-1 seronegative donors and stimulated with PHA-P (Difco, Detroit, Mich.; 10 µg/ml) and 10% IL-2 (Electronnucleonics, Silver Spring, Md.) 3 days prior to infection with HIV-1. PBMC cultures for all experiments included uninfected and infected cells without inhibitor, uninfected cells with inhibitor at the various concentrations, and infected cells in the presence of 1 µm zidovudine (azidothymidine, AZT).

With A3.5 H-Ala-boroPro suppresses HIV below detectable levels in a manner similar to the anti-HIV effect of AZT at 1 µm. Similar results were observed with the PBMC cells. Thus, inhibitors of this invention have an anti-HIV effect. Cell viability assays show that these inhibitors are not cytotoxic even at relatively high concentration ($10^{-3}$M for A3.5 cells).

Determination of DP-IV Activities in Biological Samples

The ability to determine DP-IV activities associated with cells and tissues is highly desirable. For example, it will permit correlations to be made between level of inhibition of DP-IV and the magnitude of the observed biological affect, e.g., on cell proliferation, and IL-2 production. Such correlation is helpful in establishing whether or not the biological effect is due to inhibition of DP-IV. We have found that such determinations can be reproducibly and reliably made using the readily available chromogenic substrates for DP-IV: X-Pro-p-nitroanilides and X-Pro-7-amino-4-trifluoromethyl coumarins (AFC). The AFC substrates are fluorescent and thus provide greater sensitivity. DP-IV activity is measured as release of p-nitroanilide spectrophotometrically at 410 nM, or using X-Pro-AFC derivatives and measuring fluorescence at 505 nM. Reduction in activity in the presence of inhibitor provides an easy test for inhibitory activity.

Effect of Inhibitor Stereochemistry on DP-IV Inhibition

Experiments described below demonstrate that Ala-boroPro and Pro-boroPro are potent inhibitors of DP-IV with $K_i$ values in the nanomolar range. In addition, the L,L form of Pro-boroPro is shown to be a far more potent inhibitor of DP-IV than the L,D form of Pro-boroPro.

The activity of DP-IV, isolated from porcine kidneys by the method of Wolf et al. (*ACTA Bio. Mes. Ger.* 37:409, 1972), was measured using Ala-Pro-p-nitroanilide as a substrate. Briefly, a reaction containing 50 µmol sodium Hepes (pH7.8), 10 µmol Ala-Pro-p-nitroanilide, 6 milliunits of DP-IV, and 2% (vol/vol) dimethylformamide in a total volume of 1.0 ml. The reaction was initiated by the addition of enzyme and reaction rates were measured at 25° C.

The rates of DP-IV-catalyzed hydrolysis of Ala-Pro-p-nitroanilide were determined at 3 to 5 different concentration of Ala-boroPro Pro-boroPro, boroPro and N-Boc-Ala-boroPro. In some cases, the initial reactions rates were not linear. The rates became linear after 10 min; this linear portion can be duplicated by preincubating enzyme with inhibitor for 10 min before adding substrate. Table 1 presents the results of $K_i$ measurements made over the linear range.

TABLE 1

| Inhibition constants of some inhibitors of DP-IV | |
|---|---|
| Inhibitor | $K_i$ nM |
| N-Boc-Al-boroPro | >1,000,000* |
| BoroPro | 110,000 |
| Ala-boroPro | 2 |
| Pro-boroPro | 3 |

*No inhibition detected.

Ala-boroPro was a potent inhibitor of DP-IV, having a $K_i$ value of $2\times10^{-9}$M (Table 1). Blocking the N terminus of this inhibitor (e.g., N-Boc-Ala-boroPro; Table 1) abolished inhibition, demonstrating that a free, positively charged amino group is likely essential for enzyme recognition and binding. The $K_i$ of $3\times10^{-9}$M for Pro-boroPro demonstrates that DP-IV tolerates an imino group in place of the amino functional group on the N terminus as well as the substitution of a proline side chain in place of the alanine methyl group. This shows that the S2 specificity subsite is not highly restrictive. Although DP-IV will accept nearly any amino acid at the N terminus, interactions between this amino acid and the enzyme are critical for binding. This is illustrated by the $10^5$–$10^6$ decrease in affinity on going from Ala-boroPro or Pro-boroPro to boroPro itself (Table 1).

The inhibition experiments presented in Table 1 were carried out on DP-IV isolated from pig kidneys. Pro-boroPro and Ala-boroPro inhibit DP-IV from human placenta equally well.

The Ala-boroPro and Pro-boroPro used in the experiments described above were raecemic mixtures in which the boro-Pro moiety was present as both the D-form and L-form while Ala and Pro were both the L-isomer.

High pressure liquid chromatography (HPLC) can be used to separate L-Pro-D-boroPro from L-Pro-L-boroPro. A 4.6 mm×250 mm Nucleosil C18 (5μ particle) column employing a two buffer system (Buffer A is 100% $H_2O$ with 0.1% TFA, and buffer B is 70% $CH_3CN$, 30% $H_2O$, 0.86% TFA) can be used to carry out the seperation. From 0 to 5 min 5% B and 95% A is used, and from 5 to 25 min 5% to 100% B is used. The L,L isomer comes off first at about 7 min, followed by the L,D isomer at about 10 min. NMR and mass spectra analysis were consistent with both compounds being Pro-boroPro. Rechromatography of the purified isomers indicated that the first pass on the HPLC column achieved an isomeric purity of about 99-6% for each isomer. High pressure liquid chromatography (HPLC) can similarly be used to be used to separate L-Ala-D-boroPro from L-Ala-L-boroPro or to seperate the D-boroPro form of other inhibitors from the L-boroPro form.

When L-Pro-L-boroPro and L-Pro-D-boroPro were used in a DP-IV inhibition assay, the $K_i$ for L-Pro-L-boroPro was $3.2\times10^{-11}$M while for L-Pro-D-boroPro the $K_i$ was $6.0\times10^{-8}$M. The L,L-isomer constitutes a much better inhibitor for DP-IV than the L,D-isomer. Further it is preferred that all of the amino acid residues of the DP-IV inhibitors of the invention be the L-isomer rather than the D-isomer.

Use

The inhibitory compounds can be administered in an effective amount either alone or in combination with a pharmaceutically acceptable carrier or diluent.

The above inhibitory compounds are useful for treatment of a wide variety of disease; for example, an autoimmune disease, the pathogenesis of which is dependent on T cell activity. DP-IV plays a role in such autoimmune disease and inhibition of DP-IV activity allows regulation of the progress of the disease. Such diseases include arthritis, rejection of transplanted organs, as well as SLE and AIDS. When administered to mammals (e.g., orally, topically, intramuscularly, intraperitoneally, intravenously, parenterally, nasally or by suppository), the inhibitory compounds of this invention enhance the ability of, e.g., the immune system of the mammal, to fight the disease.

Inhibitors of DP-IV can suppress IL-2 production and thus diseases in which the production of IL-2 is altered may be treated by use of these inhibitors. These inhibitors can also delay catabolism of growth hormone releasing factor, and block DP-IV activity of amoebae and microbial pathogens to allow an immune System to act more efficiently.

The inhibitory compounds or compositions can be administered alone or in combination with one another, or in combination with other therapeutic agents. The dosage level may be between 1–500 mg/kg/day.

Other Embodiments

Other embodiments are within the following claims. For example, other inhibitors can be created which mimic the structure of Ala-boroPro. Examples of such inhibitors are shown in FIG. 2 and include Ala-boroPro. These inhibitors generally have a boroPro group, or its equivalent, described above in the Summary of the Invention, and a positively charged amine group. The inhibitors are designed so that minimal interaction of the amine and boroPro groups occurs, and thus no cyclic structure is formed at pH 7.0. These inhibitors interact and/or bind with DP-IV, and thereby reduce the DP-IV enzymatic activity toward a normal substrate. These inhibitors are synthesized by procedures well known to those of ordinary skill in this art.

What is claimed is:

1. A method for treating transplant rejection in a patient comprising administering to said patient an inhibitor of DP-IV, having the structure:

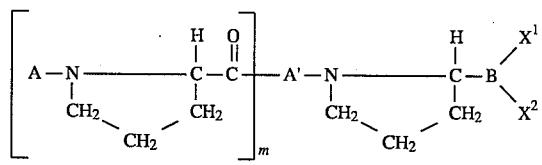

wherein m is an integer between 0 and 10, inclusive; A and A' are amino acid residues such that the A in each repeating bracketed unit can be a different amino acid residue; the bonds between A and N, A' and C, and between A' and N are peptide bonds; and each $X^1$ and $X^2$ is, independently, a hydroxyl group or a group capable of being hydrolysed to a hydroxyl group at physiological pH.

2. The method of claim 1 wherein A and A' are independently proline or alanine residues.

3. The method of claim 2 wherein m is 0.

4. The method of claim 2 wherein $X^1$ and $X^2$ are hydroxyl groups.

5. The method of claim 1 wherein the C bonded to B is in the L-configuration and A and A' are L-amino acid residues.

6. The method of claim 1 wherein said inhibitor is L-Ala-L-boroPro.

7. The method of claim 1 wherein said inhibitor is L-Pro-L-boroPro.

8. A method for treating arthritis or SLE in a patient comprising administering to said patient an inhibitor of DP-IV, having the structure:

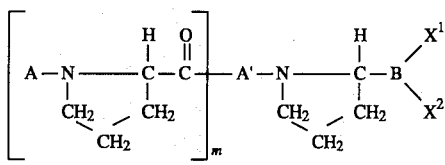

wherein m is an integer between 0 and 10, inclusive; A and A' are L-amino acid residues such that the A in each repeating bracketed unit can be a different amino acid residue; the C bonded to B is in the L-configuration; the bonds between A and N, A' and C, and between A' and N are peptide bonds; and each $X^1$ and $X^2$ is, independently, a hydroxyl group or a group capable of being hydrolysed to a hydroxyl group at physiological pH.

9. The method of claim 8 wherein A and A' are independently proline or alanine residues.

10. The method of claim 8 wherein m is 0.

11. The method of claim 8 wherein $X^1$ and $X^2$ are hydroxyl groups.

12. The method of claim 8 wherein said inhibitor is L-Ala-L-boroPro.

13. The method of claim 8 wherein said inhibitor is L-Pro-L-boroPro.

* * * * *

UNITED STATES PATENT AND TRADEMARK OFFICE
CERTIFICATE OF CORRECTION

PATENT NO. : 5,462,928

DATED : October 31, 1995

INVENTOR(S) : William W. Bachovchin, et al

It is certified that error appears in the above-indentified patent and that said Letters Patent is hereby corrected as shown below:

On the title page, under References Cited, add the following prior art:

| | | |
|---|---|---|
| 4,318,904 | Mar/9/82 | Shaw et al. |
| 4,499,082 | Feb/12/85 | Shenvi et al. |
| 4,582,821 | Apr/15/86 | Kettner et al. |
| 4,636,492 | Jan/13/87 | Kettner et al. |
| 4,652,552 | Mar/24/87 | Kettner et al. |

Bachovchin et al., J. Biol. Chem., 265:3738, 1990
Barton et al., J. Leukocyte Biol., 48:291, 1990

Column 4, line 3, "inhibitory" is misspelled;

Column 5, line 66, replace "compound I" with --compound 1 is 4-bromo-1-chlorobutyl boronate pinacol and--;

Column 6, line 6, replace "I" with --1--;

Column 6, line 9, replace "Compound II" with --Compound 2 is 4-bromo-1[(bistrmethylsilyl) amino] butyl boronate pinacol--;

UNITED STATES PATENT AND TRADEMARK OFFICE
CERTIFICATE OF CORRECTION

PATENT NO. : 5,462,928

DATED : October 31, 1995

INVENTOR(S) : William W. Bachovchin, et al

It is certified that error appears in the above-indentified patent and that said Letters Patent is hereby corrected as shown below:

Column 6, line 14, replace "I" with --1--;

Column 6, line 20, replace "compound II" with --compound 2--;

Column 6, line 21, replace "Compound III" with --Compound 3 is 1-trimethylsilyl-boroProline-pinacol--;

Column 6, line 23-24, replace "compound II" at both occurrences with ---4-bromo-1[(bistrmethylsilyl) amino] butyl boronate pinacol--;

Column 6, line 26 replace "Compound IV" with --Compound 4--;

Column 6, line 27, replace compound III" with --compound 3--;

Column 6, line 33, replace "compound II" with --4-bromo-1[(bistrmethylsilyl) amino] butyl boronate pinacol--;

Column 11, line 26, replace "seperation" with --separation--;

UNITED STATES PATENT AND TRADEMARK OFFICE
CERTIFICATE OF CORRECTION

PATENT NO. : 5,462,928
DATED : October 31, 1995
INVENTOR(S) : William W. Bachovchin, et al It is certified that error appears in the above-indentified patent and that said Letters Patent is hereby corrected as shown below:

Column 11, line 37, replace "seperation" with --separation--.

Signed and Sealed this

Seventh Day of May, 1996

Attest:

BRUCE LEHMAN

Attesting Officer     Commissioner of Patents and Trademarks